United States Patent
De Vos et al.

(10) Patent No.: US 10,806,758 B2
(45) Date of Patent: Oct. 20, 2020

(54) METHODS FOR CULTURING AND PRESERVING EUBACTERIUM HALLII AND TREATING DISEASE AND PREPARATION THEREOF

(71) Applicant: Caelus Pharmaceuticals B.V., Zegveld (NL)

(72) Inventors: Willem Meindert De Vos, Ede (NL); Jozef Franciscus Maria Louis Seegers, Leiden (NL)

(73) Assignee: Caelus Pharmaceuticals B.V., Zegveld (NL)

(*) Notice: Subject to any disclaimer, the term of this patent is extended or adjusted under 35 U.S.C. 154(b) by 71 days.

(21) Appl. No.: 16/060,902

(22) PCT Filed: Jan. 2, 2017

(86) PCT No.: PCT/NL2017/050001
§ 371 (c)(1),
(2) Date: Jun. 8, 2018

(87) PCT Pub. No.: WO2017/116235
PCT Pub. Date: Jul. 6, 2017

(65) Prior Publication Data
US 2019/0151377 A1 May 23, 2019

(30) Foreign Application Priority Data
Dec. 31, 2015 (NL) .................................... 2016055

(51) Int. Cl.
*A61K 35/741* (2015.01)
*C12N 1/20* (2006.01)
(Continued)

(52) U.S. Cl.
CPC .............. *A61K 35/741* (2013.01); *A61K 9/19* (2013.01); *C12N 1/04* (2013.01); *C12N 1/20* (2013.01); *A61K 2035/115* (2013.01)

(58) Field of Classification Search
CPC ........ A23V 2002/00; A23V 2200/3204; A23V 2200/328; A23V 2200/332; A23V 2200/3202; A23K 10/16; A23K 10/18; A23L 29/065; A23L 2/52; A23L 33/135; A23L 33/127; A61K 2035/11; A61K 35/744; A61K 9/0095; A61K 2035/115; A61K 35/741; A61K 9/19; A61K 35/74; A61K 35/742; A61K 2300/00; A61K 35/745; A61K 9/0053; A61K 31/733; A61K 45/06; A61K 35/747; A61K 9/48; A61K 9/4816; A61K 31/715; A61K 9/4891; A61K 38/13; A61K 9/2846; A61K 31/00; A61K 31/7004; A61K 31/7016; A61K 35/37; A61K 35/39; A61K 38/46; A61K 9/0031; A61K 31/4172; A61K 33/40; A61K 31/19; A61K 38/482; A61K 9/0014; A61K 9/0056; A61K 9/06; A61K 9/14; A61K 9/28; A61K 9/50; C12N 1/04; C12N 1/20; C12N 15/52; C12N 15/74; C12N 15/81; C12N 9/0004; C12N 9/0008; C12N 9/1029; C12N 9/88; A61P 1/00; A61P 43/00; A61P 3/04; A61P 3/10; A61P 1/04; A61P 1/12; A61P 29/00; A61P 17/00; A61P 31/04; A61P 25/00; A61P 37/00; A61P 3/00; A61P 31/00; A61P 37/04; A61P 35/00; A61P 1/06; A61P 1/14; A61P 1/16; A61P 3/06; A61P 5/00; Y02A 50/473; Y02A 50/402; Y02A 50/475; Y02A 50/478; Y02A 50/481; Y02A 50/48; Y02A 50/401; Y02A 50/414; Y02A 50/469; Y02A 50/49; Y02A 50/479; C12Q 1/689; C12Q 1/04; G01N 2333/605; G01N 2800/04; G01N 33/66; G01N 33/56911; C12P 13/06; C12P 13/08; C12P 7/16; C12P 7/18; C12P 7/26; C12P 7/46; C12P 7/56; C12P 7/42; C12P 7/52; C12P 7/54; C12Y 102/01003; C12Y 102/07001; C12Y 114/15003; C12Y 118/01001; C12Y 118/01002;
(Continued)

(56) References Cited

U.S. PATENT DOCUMENTS 5,902,578 A  5/1999  Halpin-Dohnalek et al.
6,224,863 B1  5/2001  Bacic et al.
(Continued)

FOREIGN PATENT DOCUMENTS

EP  1917869 A1  5/2008
EP  2573165 A1  3/2013
(Continued)

OTHER PUBLICATIONS

Wilkins-Chalgren Agar (7232) Neogen Corp. Rev. 4, 2pp. (Year: 2017).*

(Continued)

*Primary Examiner* — Deborah K Ware
(74) *Attorney, Agent, or Firm* — TraskBritt

(57) ABSTRACT

A method for culturing and preserving the probiotic gut microorganism *Eubacterium hallii* is disclosed. The method provides an *E. hallii* preparation that is suitable for administration or ingestion to humans and that provides high *E. hallii* biomass yields. Preferably, the medium used for culturing *E. hallii* to high biomass yields comprises food grade components only, is free of any animal sources, and/or is kosher. Further, including a method of treating disease using the *E. hallii* preparation.

20 Claims, No Drawings

(51) Int. Cl.
 C12N 1/04 (2006.01)
 A61K 9/19 (2006.01)
 A61K 35/00 (2006.01)
(58) Field of Classification Search
 CPC .... C12Y 203/01008; C12Y 203/01054; C12Y 401/01001; C12Y 401/02009; Y02E 50/10; Y02P 20/52; A23P 10/30; A23Y 2300/45
 See application file for complete search history.

(56) References Cited

U.S. PATENT DOCUMENTS

| | | | |
|---|---|---|---|
| 6,645,530 | B1 | 11/2003 | Borody |
| 9,433,650 | B2 | 9/2016 | Nieuwdorp et al. |
| 9,623,055 | B2 | 4/2017 | Nieuwdorp et al. |
| 2004/0076614 | A1 | 4/2004 | Schur |
| 2007/0258953 | A1 | 11/2007 | Duncan et al. |
| 2008/0069861 | A1 | 3/2008 | Brown et al. |

FOREIGN PATENT DOCUMENTS

| | | | |
|---|---|---|---|
| WO | 2004085628 | A1 | 10/2004 |
| WO | 2008076696 | A2 | 6/2008 |
| WO | 2010036876 | A2 | 4/2010 |
| WO | 2011043654 | A1 | 4/2011 |
| WO | 2011145516 | A1 | 11/2011 |
| WO | 2012142605 | A1 | 10/2012 |
| WO | 2013/032328 | A1 | 3/2013 |
| WO | 2013032328 | A1 | 3/2013 |
| WO | 2014/145958 | A2 | 9/2014 |
| WO | 2014145958 | A2 | 9/2014 |
| WO | 2016/070151 | A1 | 5/2016 |
| WO | 2016070151 | A1 | 5/2016 |
| WO | 2017116235 | A1 | 7/2017 |

OTHER PUBLICATIONS

Netherlands Search Report for Netherlands Application No. NL2016055, 10 pages, date research was completed, dated Oct. 27, 2016.
PCT International Search Report, PCT/NL2017/050001, dated Mar. 13, 2017.
PCT International Written Opinion, PCT/NL2017/050001, dated Mar. 13, 2017.
Cofman et al., A comparison of NO and N2O production by the Autotrophic Nitrifier Nitromonas europaea and the Heterotrophic Nitrifier Alcalignees faeclis, Aug. 11, 1993, pp. 3525-3533, Applied Envitonmental Microbiology, vol. 59 No. 11.
Engels et al., Frontiers Microbiol., 7(713);1-12 (2016).
Examination Report for Singapore Patent Application No. 11201401811W, dated Mar. 16, 2015.
Flint et al., Env. Microbiol., 9(5):1101-1111 (2007).
Gao et al., Diabetes, 2009, pp. 1409-1417, vol. 58.
Heenan et al., Growth Medium for Culturing Probiotic Bacteria for Applications in Vegetarian Food Products, LWT Food Science and Technology, Jan. 1, 2002, pp. 171-176, vol. 35, No. 2, Academic Press, United Kingdom.
International Search Report dated Oct. 15, 2012 for International Application No. PCT/NL2012/050592, 3 pages.
Kavuncuoglu F. et al., First Reported Case of Alcaligenes faecalis Peritonitis, Perit Dial Int., Jan.-Feb. 2010, vol. 30, No. 1, pp. 112-121.
Ma et al., J. Hepatology, 49:821-830 (2008).
Munoz-Tamayo et al., Kinetic modelling of lactate utilization and butyrate production by key human colonic bacterial species, Fems Microbiology Ecology, Apr. 18, 2011, pp. 615-623, vol. 76, No. 3.
Netherlands Search Report dated Mar. 26, 2012 for Netherlands Application No. NL2007319, 4 pages.
PCT International Search Report, PCT/EP2015/076995, dated Feb. 11, 2016.
PCT International Written Opinion, PCT/EP2015/076995, dated Feb. 11, 2016.
Suthar et al., Bacterial contamination in drinking water: a case study in rural areas of northern Rajasthan, India, Environ Monit Assess., Nov. 21, 2008, vol. 159, No. 1-4, pp. 43-40.
Williams et al., Diabetes, 2000, pp. 626-632, vol. 49.
Yun et al., J. App. Microbiol., 107:1681-1686 (2009).
Ahanci et al., Heightened efficacy of nitric oxide-based therapies in type II diabetes mellitus and metabolic syndrome, Oct. 14, 2008, pp. H2388-H2398, Am J Physical Heart Circ Physiol 295.
Anderson et al., A comparison of NO and N2O production by the Autotrophic Nitrifier Nitromonas europaea and the Heterotrophic Nitrifier Alcalignees faeclis, Aug. 11, 1993, pp. 3525-3533, Applied Environmental Microbiology, vol. 59.
Notification of Third Chinese Office Action dated Jan. 9, 2017, application No. 201280053708.2, english translation included.
Duncan et al., Lacatate-Utilizing Bacteria Isolated from Human Feces, That Produce Butyrate as a Major Fermentation Product; Jun. 14, 2004, pp. 5810-5817, Applied and Environmental Microbiology vol. 70 No. 10.
Browne et al. "Culturing of 'unculturable' human microbiota reveals novel taxa and extensive sporulation", May 2016, Nature vol. 533, p. 543-46.
Duncan et al. "Effects of Alternative Dietary Substrates on Competition between Human Colonic Bacteria in an Anaerobic Fermentor System" Applied and Environmental Microbiology, Feb. 2003, p. 1136-1142 vol. 69, No. 2.
Duncan et al. "Lactate-Utilizing Bacteria, Isolated from Human Feces, That Produce Butyrate as a Major Fermentation Product", Applied and Environmental Microbiology, Oct. 2004, p. 5810-5817 vol. 70, No. 10.
Engels et al. "The Common Gut Microbe Eubacterium hallii also Contributes to Intestinal Propionate Formation" Frontiers in Microbiology, www.frontiersin.org, May 2016, vol. 7, Article 7 (12 Pages).
Heenan et al: "Growth Medium for Culturing Probiotic Bacteria for Applications in Vegetarian Food Products",LWT—Food Science and Technology, Academic Press, United Kingdom, vol. 35, No. 2, Jan. 1, 2002 (Jan. 1, 2002), pp. 171-176.
Munoz-Tamayo et al: "Kinetic modelling of lactate utilization and butyrate production by key human colonic bacterial species", FEMS Microbiology Ecology., vol. 76, No. 3, Apr. 18, 2011 (Apr. 18, 2011) pp. 615-624.
Serna-Cock et al. "Probiotic encapsulation" African Journal of Microbiology Research, vol. 7(40), pp. 4743-4753, Oct. 4, 2013.
Bunesova et al. "Comparison of mupirocin-based media for selective enumeration of bifidobacteria in probioric supplements" Journal of Microbiological Methods (2015) vol. 109, pp. 106-109.
Japanese Notice of Reasons for Refusal for Japanese Application No. 2018-532242, dated Jul. 21, 2020, 13 pages with English translation.
Rockova et al. "Growth of bifidobacteria in mammalian milk" Czech J. Anim. Sci., 58, 2013 (3): 99-105.

* cited by examiner

METHODS FOR CULTURING AND PRESERVING *EUBACTERIUM HALLII* AND TREATING DISEASE AND PREPARATION THEREOF

CROSS-REFERENCE TO RELATED APPLICATIONS

This application is a national phase entry under 35 U.S.C. § 371 of International Patent Application PCT/NL2017/050001, filed Jan. 2, 2017, designating the United States of America and published in English as International Patent Publication WO 2017/116235 A1 on Jul. 6, 2017, which claims the benefit under Article 8 of the Patent Cooperation Treaty to Netherlands Patent Application Serial No. 2016055, filed Dec. 31, 2015.

TECHNICAL FIELD

This application is in the field of probiotics, and is particularly concerned with providing a culturing method of *E. hallii* that provides an *E. hallii* composition that is suitable for administration to humans, that gives high biomass yield, and that ideally is suitable for administration to humans regardless of their religion.

BACKGROUND

The human intestinal tract contains a large variety of microorganisms, of which bacteria are the most dominant and diverse. The microbiota is thought to be composed of 500 to 1000 different bacterial species, most of which are anaerobic. Intestinal microbiota contributes to overall metabolism and plays a role in converting food into nutrients and energy. Variations in the composition of microbiota are found between humans, and certain variations can be correlated with certain diseases or conditions.

WO2013/032328 discloses a causal role of the small intestinal microbiota in insulin resistance and dyslipidemia. Eighteen male subjects with newly diagnosed metabolic syndrome underwent small intestine biopsies and subsequent polyethylene-glycol bowel lavage through duodenal tube insertion followed by random assignment to either allogenic or autologous fecal transplantation. In the allogenic fecal transplantation group that was performed on nine subjects, the fecal material was derived from a healthy and lean donor. The autologous transplantation group included the nine other subjects and these received their own fecal material. It was found that the subjects of the allogenic group were characterized by different sigmoidal gut microbiota compared to those of the autologous group. Fasting levels of TG-rich lipoproteins (TG/ApoB ratio) were significantly reduced in the subjects in the allogenic group with no effect after autologous feces infusion. Although the weight of the subjects remained stable, six weeks after fecal transplantation, an improvement in both peripheral (Rd) and hepatic insulin sensitivity (suppression of EGP) was found in the allogenic group while no significant changes were observed in the autologous treatment group.

Changes in small intestinal microbiota between subjects receiving allogenic or autologous fecal transplantation were identified. Comparing the small intestinal microbiota composition at baseline and after six weeks, the allogenic group showed an increased abundance of the butyrate-producing *E. hallii*. Notably, *E. hallii* was almost two-fold reduced following infusion in the autologous group.

Bacteria belonging to *Eubacterium hallii* et rel. include relatively fast-growing anaerobes. They have the metabolic capacity to convert lactate into butyrate in a process that needs acetate (Munoz-Tamayo et al. 2011, *FEMS Microbiol. Ecolo.* 76:615-624). Lactate and acetate are abundant metabolites in the upper intestinal tract that is colonized by, among others, streptococci and lactobacilli that can produce these compounds (Booijink et al. 2010, vide supra).

In db/db mice (a model of obesity, diabetes, and dyslipidemia), distinct effects were found of short-term oral *E. hallii* L2-7 supplementation to the small intestine on normalization of insulin resistance (as detected by HOMA calculation and postprandial glucose metabolism by AUC of oral glucose tolerance curve), as well as fasting lipid profiles in db/db mice (WO2013/032328).

Culturing obligate anaerobic gut microorganisms is notoriously difficult, and high biomass yields are hardly ever obtained.

Hitherto, *E. hallii* has been cultured in complex media, and relatively low biomass yields have been obtained (WO2013/032328; Duncan et al., *Appl. Environm. Microbiol.* 70:5810).

There is a need in the art for a method of culturing *E. hallii*, an obligate anaerobe, that provides a composition suitable for administration to humans and that gives high biomass yields. Preferably, such composition should comprise all food grade sources, should be free of animal components, and/or should be kosher. Preferably, the culturing method is based on a simple medium.

BRIEF SUMMARY

A method of preparing an *E. hallii* preparation has been developed that is suitable for administration or ingestion to humans and that gives high biomass yields, preferably yields suitable for commercial production. Ideally, the medium comprises food grade components only, is free of any animal sources, and/or is kosher. The method of the disclosure is based on a simple medium.

Definitions

As used herein, the term "effective amount" refers to a quantity sufficient to achieve a desired therapeutic and/or prophylactic effect, e.g., an amount that results in the treatment and/or prevention of the diseases and conditions taught herein. In the context of therapeutic or prophylactic applications, the amount of *E. hallii* bacteria administered to the animal subject, preferably human subject, will depend on the type and severity of the disease or condition and on the characteristics of the subject, such as general health, age, sex, body weight and tolerance to drugs. The skilled artisan will be able to determine appropriate dosages depending on well-known factors. The bacteria can also be administered in combination with one or more additional therapeutic compounds.

In this disclosure, the verb "to comprise" and its conjugations are used in their non-limiting sense to mean that items following the word are included, but items not specifically mentioned are not excluded. In addition, the verb "to consist" may be replaced by "to consist essentially of" meaning that a composition of the disclosure may comprise additional component(s) than the ones specifically identified, the additional component(s) not altering the unique characteristics of the disclosure.

In addition, reference to an element by the indefinite article "a" or "an" does not exclude the possibility that more than one of the elements is present, unless the context clearly requires that there be one and only one of the elements. The indefinite article "a" or "an" thus usually means "at least one."

DETAILED DESCRIPTION

Methods for Culturing and Preserving *E. hallii*

This disclosure provides a method of preparing an *E. hallii* preparation suitable for ingestion by a human, the method comprising the steps of:
a) providing a medium comprising:
   about 1-100, such as about 2-80, about 4-60, preferably, about 5-40, more preferably about 10-30, g/kg of a sugar, preferably glucose;
   about 1-100, such as about 2-80, about 4-60, preferably 5-40, more preferably 10-30 g/kg of a source of nitrogen and growth factors, e.g., yeast extract;
   about 1-20, such as about 2-16, or about 3-12 g/kg plant peptone, preferably soy peptone;
   about 0.01-20, such as about 0.1-18, about 0.2-16, about 0.5-14, about 0.75-12, about 1-10, about 1.5-8, about 2-6, or about 2.5-4 g/kg of an acetate salt, such as sodium acetate;
   a buffer system maintaining the pH prior to acidification by *E. hallii* at about 6-8;
   optionally cysteine;
   optionally, magnesium ions;
   optionally, calcium ions;
   optionally, potassium ions;
   optionally, vitamins;
b) inoculating the medium with *E. hallii*;
c) allowing the *E. hallii* to grow in the medium; and
d) harvesting the *E. hallii* preparation from the medium.

The medium may comprise about 1-100, such as about 2-80, about 4-60, preferably, about 5-40, more preferably, about 10-30, g/kg of a sugar. The sugar may be selected from the group consisting of glucose, sucrose, galactose, fructose, maltose, and lactose, or any combination thereof. The medium preferably comprises about 1-100, such as about 2-80, about 4-60, preferably about 5-40, more preferably about 10-30, g/kg of glucose, fructose or sucrose as a carbon source.

The medium may further comprise about 1-100, such as about 2-80, about 4-60, preferably 5-40, more preferably 10-30 g/kg of a source of nitrogen and growth factors such as yeast extract.

The medium taught herein may further comprise from about 0.1-50, such as about 0.5-40, about 1-20, about 2-16, or about 3-12 g/kg of a plant peptone. A plant peptone is a plant protein hydrolysate. It may be derived from any plant. The plant peptone may, for example, and without limitation, be selected from the group consisting of soy peptone, wheat peptone, cotton peptone, pea peptone, broadbean peptone, lupin peptone, and potato peptone. The medium may, for example, comprise from about 0.1-50, such as about 0.5-40, about 1-20, about 2-16, or about 3-12 g/kg of a soy peptone.

The medium taught herein further comprises about 0.01-20, such as about 0.1-18, about 0.2-16, about 0.5-14, about 0.75-12, about 1-10, about 1.5-8, about 2-6, or about 2.5-4 g/kg of an acetate salt. The acetate salt is important as it forms a substrate for butyrate formation by *E. hallii*. Additionally, acetate is an anti-foaming compound. The acetate salt may, without limitation, be selected from the group consisting of sodium acetate, aluminium acetate, ammonium acetate, and potassium acetate, or any combination thereof. In an embodiment, the medium comprises about 0.01-20, such as about 0.1-18, about 0.2-16, about 0.5-14, about 0.75-12, about 1-10, about 1.5-8, about 2-6, or about 2.5-4 g/kg of sodium acetate.

The medium may further comprise a buffer system that maintains the pH of the medium at about 6-8 prior to acidification by *E. hallii*. A suitable buffer system may include sodium bicarbonate, dipotassium HydrogenP and Potassium diHydrogenP as taught herein. The skilled person is perfectly capable of selecting a suitable food grade buffer system for application in the method of this disclosure.

The medium may further comprise cysteine to render the medium in a reducing state, magnesium ions, calcium ions, potassium ions, and/or vitamins. It was found that the addition of these compounds to the medium taught herein improved biomass yield even further.

In an embodiment, the medium used comprises about 1-100, such as about 2-80, about 4-60, preferably about 5-40, more preferably about 10-30, g/kg glucose; about 1-100, such as about 2-80, about 4-60, preferably 5-40, more preferably 10-30 g/kg yeast extract; about 1-20, such as about 2-16, or about 3-12 g/kg soy peptone; about 0.01-20, such as about 0.1-18, about 0.2-16, about 0.5-14, about 0.75-12, about 1-10, about 1.5-8, about 2-6, or about 2.5-4 g/kg of an acetate salt, e.g., sodium acetate; a buffer system maintaining the pH prior to acidification by *E. hallii* at about 6-8; optionally, cysteine; optionally, magnesium ions; optionally, calcium ions; optionally, potassium ions; and, optionally, vitamins.

The *E. hallii* strain used in the method taught herein may be any human *E. hallii* isolate, such as the *E. hallii* strain designated L2-7, which has been deposited at DSMZ and received deposit no. 17630.

Preferably, the medium is free of any animal sources, such as animal products or animal-derived products.

The method taught herein is preferably carried out under anaerobic conditions. Since *E. hallii* is an obligate anaerobic bacterium, its viability is affected by contact with air. Anaerobic conditions may be maintained using well-known methods, which include $N_2$ flushing.

The method as taught herein is preferably carried out at a temperature in the range of 30° C.-42° C., preferably in the range of 34° C.-40° C.

The *E. hallii* preparation may be harvested from the medium using any technique known to the skilled person, particularly a harvesting technique that is amenable to being carried out under anaerobic conditions, such as filtration.

To remove or dilute further medium components, harvested *E. hallii* cells may be washed with a physiologically acceptable solution, such as a phosphate-buffered saline solution. The skilled person is capable of selecting a suitable physiologically acceptable solution, as well as a washing method achieving the desired result. For example, diafiltration may be used to wash the *E. hallii* cells. Alternatively, the *E. hallii* cells can be centrifuged and resuspended in washing buffer, or they may be directly taken up in a buffer containing cryoprotectants and oxygen scavengers.

The method taught herein may further comprise the step of lyophilizing *E. hallii* to obtain a lyophilized *E. hallii* preparation. Alternatively or additionally, the method may further comprise the step of encapsulating *E. hallii* to obtain an encapsulated *E. hallii* preparation.

The technique of encapsulation is well known in the art for preserving probiotic bacteria (e.g., as reviewed by Serna-Cock and Vallejo-Castillo, 2013, *Afr. J. of Microbiol. Res.* 7(40):4743-4753, herein incorporated by reference). Any of the preservation techniques and preservation systems taught by Serna-Cock and Vallejo-Castillo may be employed in the present disclosure.

The lyophilizing step may be carried out using any method known in the art. Freeze-drying or lyophilization is commonly used to preserve microorganisms. After all, lyophilisates can be stored for decades. Accordingly, many microbes are stored as lyophilisates in strain collections. To overcome the potential viability loss during formulation, it is generally recommended to lyophilize concentrated cultures, e.g., containing at least $10^7$ cells. This ensures the presence of sufficient viable cells after lyophilization, long-term storage and reconstitution. For probiotic preparations such as the E. hallii preparations taught herein, it is important that as many bacteria as possible survive lyophilization and subsequent storage.

It was found that E. hallii is extremely sensitive to freezing and freeze-drying. Cryoprotectants are often employed to protect probiotic formulations during lyophilization and to enhance shelf-life. However, the selection of appropriate and compatible cryopreservants has remained a major challenge. Hitherto, no suitable cryoprotectants have been reported for E. hallii.

In the method taught herein, a cryoprotectant selected from the group consisting of sucrose, maltose, maltodextrin, trehalose, mannitol, sorbitol, inulin, glycerol, DMSO, ethylene glycol, propylene glycol, 2-methyl-2,4-pentanediol, polyethylene glycol, polyvinylpyrrolidone, polyvinyl alcohol, polyglycerol, skim milk powder, milk protein, whey protein, UHT milk, betaine, adonitol, sucrose, glucose, lactose or any combination thereof, may be employed.

Prebiotics such as starch and wheat bran may further be added before lyophilization to enhance the efficacy of the E. hallii preparation taught herein. Addition of antioxidants such as riboflavin, riboflavin phosphate or a physiologically acceptable salt thereof, glutathione, ascorbate, glutathion and cysteine to the lyophilization mixture may further enhance the viability of the E. hallii preparation taught herein during storage.

Lyophilization methods include, without limitation, slow, gradual freezing to −40° C. before drying, rapid freezing by placing at −80° C. before drying, or ultra rapid freezing by dripping cells with cryoprotector in liquid nitrogen before drying.

In order to render E. hallii more resistant to freezing, it may be beneficial to subject the E. hallii cells to mild to moderate stress treatments during culturing to prepare these for adverse conditions. For example, during culturing, the cells may be subjected to mild oxidative stress, e.g., by adding a low dose of hydrogen peroxide, by limiting certain nutrient, by culturing at low pH value, and the like.

E. hallii Preparation

This disclosure also relates to an E. hallii preparation obtainable by the method as taught herein. Preparation is characterized by being suitable for ingestion by a human.

The E. hallii preparation taught herein preferably comprises an effective amount of E. hallii, in conjunction with a physiologically acceptable carrier.

Preferably, the E. hallii preparation comprises between about $10^6$ and about $10^{12}$, preferably between about $10^8$ and about $10^{12}$, viable E. hallii bacteria. Preferably, the bacteria are contained in a daily dose.

Preferably, the E. hallii preparation taught herein is for enteral or oral administration. A composition for enteral or oral administration may be either a food composition, feed composition, or a pharmaceutical composition.

The E. hallii preparation taught herein will usually comprise a carrier, such as a pharmaceutical carrier, preferably an inert carrier. The preferred form depends on the intended mode of administration and (therapeutic) application. A pharmaceutical carrier can be any compatible, nontoxic substance suitable to deliver E. hallii bacteria to the gastro-intestinal-tract of a subject. For example, sterile water, or inert solids may be used as a carrier usually complemented with a pharmaceutically acceptable adjuvant, buffering agent, dispersing agent, and the like. A composition will either be in liquid form, e.g., a stabilized suspension of E. hallii bacteria, or in solid form, e.g., a powder of lyophilized E. hallii bacteria. For oral administration, E. hallii bacteria can be administered in solid dosage forms, such as capsules, tablets, and powders, or in liquid dosage forms, such as elixirs, syrups, and suspensions. E. hallii bacteria may, for example, be encapsulated in capsules such as gelatin capsules, together with inactive ingredients and powdered carriers, such as, e.g., glucose, lactose, sucrose, mannitol, starch, cellulose or cellulose derivatives, magnesium stearate, stearic acid, sodium saccharin, talcum, magnesium carbonate and the like.

The E. hallii preparation taught herein may be in the form of a food supplement or a food or food composition (herein jointly referred to as "food composition"), which may, besides E. hallii bacteria, also contain a suitable food base. Alternatively, such preparation may be in the form of a feed supplement or a fodder or feed composition (herein jointly referred to as "feed composition"). A food or food composition or feed composition is herein understood to include a liquid for human or non-human animal consumption, i.e., a drink or beverage. A food or food composition or feed composition may be a solid, semi-solid and/or liquid food or food composition and, in particular, may be a dairy product, such as a fermented dairy product including, but not limited to, a yogurt, a yogurt-based drink or buttermilk. Such a food or food composition or feed composition may be prepared in a manner known per se, for example, by adding E. hallii bacteria to a suitable food, food base, or feed base, in a suitable amount. Similarly, this may include the use of these bacteria in capsulated form as described above since they have to pass the low pH of the stomach. This may also be a preferred way as to reduce the traces of butyrate that are associated with the growth of E. hallii bacteria and may produce off-flavor in a food or food composition. In another embodiment, E. hallii bacteria may be used in or for the preparation of a food or food composition or feed composition, e.g., by fermentation. In doing so, E. hallii bacteria may be used in a manner known per se for the preparation of such fermented foods or food compositions or fermented feed compositions, e.g., in a manner known per se for the preparation of fermented dairy products using lactic acid bacteria. In such methods, E. hallii bacteria may be used in addition to a micro-organism usually used, and/or may replace one or more or part of a micro-organism usually used.

Preferably, the E. hallii preparation taught herein may contain E. hallii bacteria in amounts that allow for convenient (oral) administration as indicated above, e.g., or in one or more doses per day or per week. In particular, a preparation may contain a unit dose of E. hallii.

E. hallii preparation is suitable for use as a medicament, particularly for use in preventing and/or treating insulin resistance and/or insulin resistance-related complications such as metabolic syndrome, dyslipidemia, type 2 diabetes mellitus, non-alcoholic fatty liver disease (NAFLD) or non-alcoholic steatosis hepatis (NASH), and insulin resistance in endocrine diseases (e.g., obese subjects with type 1 diabetes mellitus, Cushing's disease and lipodystrophy syndromes), for preventing and/or treating lactic-acidosis, short bowel syndrome or inflammatory bowel disease, and for preventing, reducing the incidence or reducing the severity of colorectal cancer or colitis.

This disclosure also teaches a method of promoting butyric acid formation in the intestine of a mammal, the method comprising the step of administering an *E. hallii* preparation as taught herein to a subject in need thereof.

All patent and literature references cited in the present specification are hereby incorporated by reference in their entirety.

It will be clear that the above description is included to illustrate some embodiments of the disclosure and not to limit the scope of protection. Starting from this disclosure, many more embodiments that are within the scope of protection and the essence of this disclosure and that are obvious combinations of prior art techniques and the disclosure of this application, will be evident to a skilled person.

EXAMPLES

Example 1

Culturing of *E. hallii*

Medium was prepared using the following components and concentrations:

Medium 1

| Component | Concentration (g/kg) |
| --- | --- |
| Yeast extract | 20 |
| Soy peptone Amisoy BF | 4 |
| Sodium bicarbonate | 8 |
| Sodium acetate | 2.7 |
| dipotassium HydrogenP | 0.9 |
| Potassium diHydrogenP | 0.9 |
| Ammonium chloride | 0.9 |
| Sodium chloride | 0.9 |
| Glucose | 20 |
| Demi water | 940 |

The medium was subjected to autoclavation for 20 minutes at 121° C., followed by flushing with $N_2$. The pH was adjusted to 6.9±0.1.

About 20 ml lab culture of *E. hallii* was added to about 1 L of medium and cultured during 18 hours at 37° C. 500 ml of this culture was subsequently added to 20 L of media, and cultured during 14-18 hours at 37° C. All steps were executed aseptically and under $N_2$ (flush).

Cells grew to an optical density ($OD_{600}$) of 8.5 while acidifying the medium from pH 6.9 to pH 5.0.

Example 2

Medium 2

| Component | Concentration (g/kg) |
| --- | --- |
| Yeast extract | 20 |
| Soy peptone Amisoy BF | 4 |
| Sodium bicarbonate | 8 |
| Sodium acetate | 2.7 |
| dipotassium HydrogenP | 0.9 |
| Potassium diHydrogenP | 0.9 |
| Ammonium chloride | 0.9 |
| Sodium chloride | 0.9 |
| Magnesium sulphate | 0.9 |
| Calcium chloride | 0.26 |
| Glucose | 20 |
| Demi water | 940 |

To medium 2, the following filter-sterilized anaerobic solutions were added:

| | |
| --- | --- |
| Cysteine, $N_2$ degassed | 0.05% |
| Vitamin solution I (1000 x concentrated), $N_2$ degassed | 1 |

Vitamin solution I (1000× concentrated)

| | |
| --- | --- |
| Biotin | 10 mg |
| Cobalamin | 10 mg |
| PABA | 30 mg |
| Folic acid | 50 mg |
| Pyridoxamine | 150 mg |
| Demi water | 1 L |

The medium was subjected to autoclavation for 20 minutes at 121° C., followed by flushing with $N_2$. The pH was adjusted to 6.9±0.1.

About 20 ml lab culture of *E. hallii* was added to about 1 L of medium and cultured during 18 hours at 37° C. 500 ml of this culture was subsequently added to 20 L of medium, and cultured during 14-18 hours at 37° C. 10 L of the culture was added to 320 L of medium and cultured during 14-16 hours at 37° C. All steps were executed aseptically and under $N_2$ (flush).

Cells grew to an optical density ($OD_{600}$) of 9.4 ($1.4 \times 10^9$ cells/ml) while acidifying the medium from pH 6.9 to pH 5.0.

The cells were harvested using concentration with hollow fiber membranes (Koch membrane systems; HF3043-25-43-PM500; HF3043-16-106-PM500) and diafiltration using PBS. Diafiltration continued until the level of medium components and fermentation products reached about 2% of their initial concentration. The sample was concentrated about 20-fold, yielding about 15 L of concentrated *E. hallii* cells in PBS. About 99.8% of the medium compounds were removed.

Samples were filled inside a disinfected laminar flow cabinet either in glycerol or in glycerol and PBS (pre-autoclaved, pre-cooled and pre-flushed with $N_2$).

Freeze-Drying of Cells

Centrifugation bowls comprising 800 mL end culture were centrifuged at 4000 $rpm^{-1}$ for 30 minutes. The supernatant was removed in an anaerobic chamber.

Subsequently, the *E. hallii* cells were lyophilized. Five different cryoprotectant solutions were tested:

Cryoprotectant solution 1:

|  | Concentration (g/L) |
| --- | --- |
| Maltodextrine | 100 |
| Trehalose | 100 |
| L-cysteine HCl | 9 |
| Water |  |

Cryoprotectant solution 2:

|  | Concentration (g/L) |
| --- | --- |
| Mannitol | 100 |
| Trehalose | 100 |
| L-cysteine HCl | 9 |
| Water |  |

Cryoprotectant solution 3:

|  | Concentration (g/L) |
| --- | --- |
| Sucrose | 100 |
| Mannitol | 100 |
| Water |  |

Cryoprotectant solution 4:

|  | Concentration (g/L) |
| --- | --- |
| Sucrose | 150 |
| Maltose | 150 |
| Water |  |

Cryoprotectant solution 5:

|  | Concentration (g/L) |
| --- | --- |
| Sucrose | 100 |
| Trehalose | 100 |
| Water |  |

80 mL cryoprotectant solution was added to the centrifugation bowl containing cell pellet. The bowls were shaken in order to homogenize the biomass and cryoprotectant solution. The resultant was spread in two plates containing 50 mL in an anaerobic chamber. These plates were put in a hermetically sealed box and deep-frozen at −40° C. The plates were left in the freeze-dryer for 1 to 2 days. After collection, lyophilisates were ground manually and packed in bags under anaerobic conditions. Afterwards, they were stored at −4° C.

*E. hallii* could be re-grown after lyophilization, demonstrating that the bacteria remained viable after lyophilization. In this example, the highest viability following lyophilization was found for cryoprotectant solution 1. It was found that viability of the lyophilisates were better when the entire process was carried out under anaerobic conditions to the extent possible.

Example 3—Comparative Example

The growth yields on the kosher media described in Examples 1 and 2 were much higher than those described for growth of *E. hallii* on conventional media, which contained components from animal sources. A typical example is YCFA medium as described by Duncan et al. 2003 (*Appl. Environ. Microbiol.* 69:1136-42) with added glucose or lactate. This YCFA medium is widely used to support growth of anaerobic and intestinal bacteria (see Browne et al. 2016, *Nature* 533:543-46). However, the growth of *E. hallii* L2-7 was described to reach only an $OD_{600}$ of 0.8-1.0 on YCFA with added glucose or other compounds (Duncan et al. 2004, *Appl. Environ. Microbiol.* 70:5810-17). When the animal-derived products hemin and casitone were added to YCFA with glucose, the growth was only slightly better and a maximum $OD_{600}$ of 1.8 was reached (Engels et al. 2016, *Front. Microbiol.* 7:713).

It should also be noted that the growth yield described above of an $OD_{600}$ for medium 2 of 9.4 was obtained from not yet fully outgrown cultures. To show that the developed kosher media are superior to other hitherto described media, *E. hallii* strain L2-7 was cultured for 35-40 hours in 200 ml volume of medium 2 in anaerobic chambers (Exp #1 and Exp #2; see Table below). Moreover, *E. hallii* L2-7 was also grown on a large scale in a 2.5 liter fermenter on medium 2 (Exp 2.5 liter; see Table below). The results show that on small- and large-scale fermentation, high yields of $OD_{600}$ close to 20 can be obtained.

Translating the $OD_{600}$ to a specific number of cells is dependent on several factors. The number of cells was determined by flow cytometry and an $OD_{600}$ of 1 was found to correspond to approximately $1 \times 10^8$-$1.3 \times 10^8$ cells per ml. However, it is not only the number of cells that determines the yield but also the size of the cells. It is known that the dimensions of *E. hallii* can vary considerably and cells have been described to be 0.8-2.4 micrometers in diameter and 4.7 to 25.0 micrometers in length (P. De Vos et al., *Bergey's Manual of Systematic Bacteriology*, Volume 3 Sec. Ed. p. 881). Phase contrast microscopy showed cells grown in medium 2 to be rather long, resulting in relatively low cell counts per $OD_{600}$ unit. Hence, in the comparative experiments, $OD_{600}$ values were used.

Growth of *E. hallii* L2-7

| Experiment | $OD_{600}$ |
| --- | --- |
| Exp #1 | 16.2 |
| Exp #2 | 19.5 |
| Exp #2.5 L | 17.2 |

The usefulness of the media taught herein in supporting growth of *E. hallii* was also illustrated by the observation that efficient growth of single cells was obtained on medium 2 supplemented with 1% agar with a high efficiency of plating (over 10%). It is notoriously difficult to enumerate anaerobes and usually most probable number (MPN) approaches are used to estimate the number of viable cells, which is a tedious procedure. Moreover, the usefulness of a medium that supported a high plating efficiency of *E. hallii* was also used to select for derivatives or mutants of *E. hallii* strain L2-7.

This all shows the usefulness of the media taught herein that allow efficient growth to high density of *E. hallii*.

The invention claimed is:
1. A method of preparing an *Eubacterium hallii* preparation suitable for ingestion by a human, said method comprising the steps of:
   a) providing a medium comprising:
      1-100 g/kg of a sugar,
      1-100 g/kg of a source of nitrogen and growth factors,

0.1-50 g/kg plant peptone,
acetate,
a buffer system at pH 6-8,
optionally, cysteine,
optionally, magnesium ions,
optionally, calcium ions,
optionally, potassium ions, and
optionally, vitamins;
b) inoculating said medium with E. *hallii*;
c) allowing said E. *hallii* to grow in said medium; and
d) harvesting said E. *hallii* preparation from said medium.

2. The method of claim 1, which is carried out under anaerobic conditions.

3. The method of claim 1, which is carried out at a temperature in the range of 30-42° C.

4. The method of claim 1, wherein said E. *hallii* preparation is harvested from said medium using filtration.

5. The method of claim 4, wherein the filtrate is further washed with phosphate buffered saline solution.

6. The method of claim 1, which further comprises the step of lyophilizing said E. *hallii* to obtain a lyophilized E. *hallii* preparation.

7. The method of claim 6, wherein said lyophilizing is carried out using a cryoprotectant selected from the group consisting of sucrose, maltose, maltodextrin, trehalose, mannitol, glycerol, DMSO, ethylene glycol, propylene glycol, 2-methyl-2,4-pentanediol, polyethylene glycol, polyvinylpyrrolidone, polyvinyl alcohol, polyglycerol, and any combination thereof.

8. The method according to claim 1, wherein the medium comprises:
from 5 to 40 g/kg of sugar.

9. The method according to claim 1, wherein the medium comprises:
from 5 to 40 g/kg of a source of nitrogen and growth factors.

10. The method according to claim 1, wherein the sugar is glucose.

11. The method according to claim 1, wherein the source of nitrogen and growth factors is yeast extract.

12. The method according to claim 1, wherein the plant peptone is soy peptone.

13. The method according to claim 3, wherein the temperature is in the range of 34-40° C.

14. The method according to claim 2, carried out at a temperature in the range of 30-42° C.

15. The method according to claim 14, wherein the E. *hallii* preparation is harvested from the medium utilizing filtration.

16. The method according to claim 15, wherein the filtrate is further washed with phosphate buffered saline solution.

17. *Eubacterium hallii* preparation prepared by the method of claim 1, wherein the E. *hallii* preparation comprises medium comprising:
sugar,
a source of nitrogen and growth factors,
plant peptone, and
acetate.

18. A medicament comprising the E. *hallii* preparation of claim 17.

19. A method of treating insulin resistance and/or insulin resistance-related complications, metabolic syndrome, dyslipidemia, type 2 diabetes mellitus, non-alcoholic fatty liver disease (NAFLD) or non-alcoholic steatosis hepatitis (NASH), and insulin resistance in endocrine diseases, or for treating lactic-acidosis, short bowel syndrome or inflammatory bowel disease, or reducing the incidence or reducing the severity of colorectal cancer or colitis in a subject, the method comprising:
administering to the subject the E. *hallii* preparation of claim 17.

20. A method to promote butyric acid formation in the intestine of a mammal, said method comprising the step of administering an E. *hallii* preparation according to claim 17 to a subject in need thereof.

* * * * *